US00PP30408P3

(12) United States Plant Patent
Hoogkamp

(10) Patent No.: US PP30,408 P3
(45) Date of Patent: Apr. 16, 2019

(54) ***CURCUMA* PLANT NAMED 'CURHALAWI'**

(50) Latin Name: *Curcuma alismatifolia*
Varietal Denomination: Curhalawi

(71) Applicant: Timothy Johan Herman Hoogkamp, Doetinchem (NL)

(72) Inventor: Timothy Johan Herman Hoogkamp, Doetinchem (NL)

(73) Assignee: Nubilus B.V., Naaldwijk (NL)

( * ) Notice: Subject to any disclaimer, the term of this patent is extended or adjusted under 35 U.S.C. 154(b) by 0 days.

(21) Appl. No.: 15/932,756

(22) Filed: Apr. 20, 2018

(65) Prior Publication Data

US 2018/0317363 P1 Nov. 1, 2018

Related U.S. Application Data

(60) Provisional application No. 62/602,663, filed on May 1, 2017.

(51) Int. Cl.
*A01H 5/02* (2018.01)
*A01H 6/00* (2018.01)

(52) U.S. Cl.
USPC ..... Plt./421
CPC ..... *A01H 6/00* (2018.05); *A01H 5/02* (2013.01)

(58) Field of Classification Search
USPC ..... Plt./421
See application file for complete search history.

*Primary Examiner* — Annette H Para
(74) *Attorney, Agent, or Firm* — C. A. Whealy

(57) ABSTRACT

A new and distinct cultivar of *Curcuma* plant named 'Curhalawi', characterized by its upright and columnar plant habit with outwardly arching leaves; freely clumping growth habit; leaves with dark brown-colored midveins; freely flowering habit; and flowers with white-colored flower bracts that are positioned just above the foliar plane on strong and erect peduncles.

2 Drawing Sheets

Botanical designation: *Curcuma alismatifolia.*
Cultivar denomination: 'CURHALAWI'.

BACKGROUND OF THE INVENTION

The present invention relates to a new and distinct cultivar of *Curcuma* plant, botanically known as *Curcuma alismatifolia* and hereinafter referred to by the name 'Curhalawi'.

The new *Curcuma* plant is a product of a controlled breeding program conducted by the Inventor in Naaldwijk, The Netherlands. The objective of the breeding program is to create new *Curcumas* that have uniform plant habit, good container performance and attractive inflorescence coloration.

The new *Curcuma* plant originated from a cross-pollination made by the Inventor in July, 2011 in Naaldwijk, The Netherlands of a proprietary selection of *Curcuma alismatifolia* identified as code number 20071824-002, not patented, as the female, or seed, parent with a proprietary selection of *Curcuma alismatifolia* identified as code number 20051899-001, not patented, as the male, or pollen, parent. The new *Curcuma* plant was discovered and selected by the Inventor as a single flowering plant within the progeny of the stated cross-pollination in a controlled greenhouse environment in Naaldwijk, The Netherlands in August, 2012.

Asexual reproduction of the new *Curcuma* plant by axillary meristem culture in a controlled environment in Naaldwijk, The Netherlands since January, 2014 has shown that the unique features of this new *Curcuma* plant are stable and reproduced true to type in successive generations of asexual reproduction.

SUMMARY OF THE INVENTION

Plants of the new *Curcuma* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Curhalawi'. These characteristics in combination distinguish 'Curhalawi' as a new and distinct *Curcuma* plant:

1. Upright and columnar plant habit with outwardly arching leaves.
2. Freely clumping growth habit.
3. Leaves with dark brown-colored midveins.
4. Freely flowering habit.
5. Flowers with white-colored flower bracts that are positioned just above the foliar plane on strong and erect peduncles.

Plants of the new *Curcuma* differ from plants of the female parent selection in the following characteristics:

1. Flowers of plants of the new *Curcuma* are larger than flowers of plants of the female parent selection.
2. Plants of the new *Curcuma* have larger flower bract apices than plants of the female parent selection.

Plants of the new *Curcuma* differ from plants of the male parent selection in the following characteristics:

1. Plants of the new *Curcuma* are more freely clumping than plants of the male parent selection.
2. Plants of the new *Curcuma* and the male parent selection differ in flower bract color as plants of the male parent selection have light pink-colored flower bracts.

Plants of the new *Curcuma* can also be compared to plants of *Curcuma alismatifolia* 'Curblafu', not patented. In sideby-side comparisons plants of the new *Curcuma* differ from plants of 'Curblafu' in the following characteristics:

1. Plants of the new *Curcuma* are more freely clumping than plants of 'Curblafu'.
2. Plants of the new *Curcuma* have longer leaves than plants of 'Curblafu'.
3. Plants of the new *Curcuma* have longer postproduction longevity than plants of 'Curblafu'.

BRIEF DESCRIPTION OF THE PHOTOGRAPHS

The accompanying photographs illustrate the overall appearance of the new *Curcuma* showing the colors as true as it is reasonably possible to obtain in colored reproductions of this type. Colors in the photographs may differ slightly from the color values cited in the detailed botanical description which accurately describe the colors of the new *Curcuma* plant.

The photograph on the first sheet is a side perspective view of a typical plant of 'Curhalawi' grown in a container.

The photograph on the second sheet is a close-up view of a typical inflorescence of 'Curhalawi'.

DETAILED BOTANICAL DESCRIPTION

The aforementioned photographs and following observations and measurements describe plants grown during the spring and summer in 17-cm containers in a glass-covered greenhouse in Naaldwijk, The Netherlands and under cultural practices typical of commercial *Curcuma* production. During the production of the plants, day temperatures ranged from 22° C. to 28° C., night temperatures ranged from 20° C. to 22° C. and light levels averaged 55 kilolux. Plants were 19 weeks old when the photographs and the detailed description were taken. In the following description, color references are made to The Royal Horticultural Society Colour Chart, 2015 Edition, except where general terms of ordinary dictionary significance are used.

Botanical classification: *Curcuma alismatifolia* 'Curhalawi'.

Parentage:

*Female, or seed, parent.*—Proprietary selection of *Curcuma alismatifolia* identified as code number 20071824-002, not patented.

*Male, or pollen, parent.*—Proprietary selection of *Curcuma alismatifolia* identified as code number 20051899-001, not patented.

Propagation:

*Type.*—By axillary meristem culture.

*Time to initiate roots.*—About ten days at temperatures about 23° C.

*Time to produce a rooted young plant.*—About 28 to 30 days at temperatures about 21° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Moderately branching, medium density.

Plant description:

*Plant and growth habit.*—Upright and columnar plant habit with outwardly arching leaves; freely clumping habit with about 16 basal shoots forming per plant; moderately vigorous to vigorous.

*Plant height (soil level to top of inflorescences).*—About 66.9 cm.

*Plant diameter.*—About 80.3 cm.

Leaf description:

*Leaf arrangement.*—Alternate; simple.

*Length, fully expanded.*—About 73.3 cm.

*Width, fully expanded.*—About 5.4 cm.

*Shape.*—Narrowly oblanceolate.

*Apex.*—Acuminate.

*Base.*—Sheathing.

*Margin.*—Entire.

*Venation.*—Parallel.

*Aspect.*—Initially upright, then about 45° from vertical.

*Texture and luster, upper and lower surfaces.*—Smooth, glabrous; matte.

*Color.*—Developing leaves, upper and lower surfaces: Close to 143C and 144B. Fully expanded leaves, upper surface: Close to 137A; midvein, close to 200C; secondary venation, close to 137A. Fully expanded leaves, lower surface: Close to NN137D; venation, close to NN137D.

*Leaf sheaths.*—Length: About 22.2 cm. Width: About 6 mm. Height: About 7 mm. Texture and luster, upper surface: Smooth, glabrous; moderately glossy. Texture and luster, lower surface: Smooth, glabrous; slightly glossy. Color, upper and lower surfaces: Close to 143C; at the edges, close to 145D; venation, close to 143C.

Inflorescence description:

*Arrangement.*—Dense and upright terminal spike inflorescences developing directly from the basal shoots with numerous showy flower bracts; typically each spike with about ten clusters each with three flowers; about 180 flowers developing per plant.

*Time to flower.*—In The Netherlands, plants flower from spring into autumn; flowering continuous during this period; plants begin flowering about 13 to 17 weeks after planting.

*Flower longevity.*—Flowers last about three days on the plant; flowers not persistent; plants maintain good substance for about 40 days.

*Fragrance.*—Faint; sweet and somewhat spicy.

*Flower buds.*—Length: About 3.7 cm. Diameter: About 9 mm. Shape: Spatulate to oblanceolate. Texture and luster: Smooth, glabrous; glossy. Color: Close to N155A; towards the apex, tinged with close to 90D.

*Inflorescence length.*—About 15.5 cm.

*Inflorescence diameter.*—About 11 cm.

*Flowers.*—Length: About 4.6 cm. Diameter: About 1.5 cm by 2 cm. Shape: Zygomorphic with three petals fused towards the base; dorsal petal (labellum) is conspicuous and two smaller lateral petals; calyx with three sepals fused at the base.

*Petals.*—Length, dorsal petal: About 4.5 cm. Length, lateral petals: About 4.4 cm. Width, dorsal petal: About 1.5 cm. Width, lateral petals: About 7 mm. Shape, dorsal petal: Spatulate with praemorse apex. Shape, lateral petals: Narrowly obovate with obtuse apex. Texture and luster, all petals, upper surface: Smooth, glabrous; matte. Texture and luster, all petals, lower surface: Smooth, glabrous; slightly glossy. Color: When opening and fully opened, dorsal petal, upper surface: Close to N82B fading towards the base to close to NN155D; central stripe, close to 14A; with development, color becoming closer to 71A fading towards the base to close to 69A to 69B to lighter than 69A to 69B. When opening and fully opened, lateral petals, upper surface: Close to NN155D; with development, color becoming closer to 69A to 69B to lighter than 69A to 69B. When opening and fully opened, dorsal petal, lower surface: Close to 85D fading towards the base to close to NN155D; towards the apex and edges, close to N82A and N82B; with development, color becoming closer to 71A fading towards the base to close to 69A to 69B to lighter than 69A to 69B. When opening and fully opened, lateral petals, lower surface: Close to NN155D; with development, color becoming closer to 69A to 69B to lighter than 69A to 69B.

*Sepals.*—Length: About 4 cm. Width: About 8 mm. Shape: Narrowly obovate with obtuse apex. Texture and luster, upper and lower surfaces: Smooth, glabrous; matte. Color: When opening, upper and lower surfaces: Close to NN155D. Fully opened, upper and lower surfaces: lose to NN155D.

*Flower bracts.*—Quantity: About ten upper bracts and about ten lower bracts per inflorescence. Length, upper bracts: About 8 cm. Width, upper bracts: About 3.7 cm. Length, lower bracts: About 4 cm. Width, upper bracts: About 4.5 cm. Shape, upper bracts: Ovate, very slightly concave. Shape, lower bracts: Broadly obovate; strongly concave. Apex, upper bracts: Acute. Apex, lower bracts: Obtuse. Base, all bracts: Fused. Margin, upper bracts: Entire. Margin, lower bracts: Entire; undulate. Texture and luster, upper bracts, upper and lower surfaces: Smooth, glabrous; slightly glossy. Texture and luster, lower bracts, upper and lower surfaces: Smooth, glabrous; slightly glossy. Color: Upper bracts, upper surface: Close to NN155B and 157D; towards the base, and apex, close to 145B. Lower bracts, upper surface: Close to 143C; distally, close to 143B. Upper bracts, lower surface: Close to NN155B slightly tinged with close to 157D; towards the base and apex, close to 145B. Lower bracts, lower surface: Close to 143C.

*Peduncles.*—Length: About 51.2 cm. Diameter: About 6 mm. Strength: Strong. Texture and luster: Smooth, glabrous; matte. Angle: Upright, erect. Color: Close to 137B.

*Stamens.*—Quantity: Two per flower. Filament length: About 1.5 cm. Filament diameter: About 5 mm. Filament color: Close to 84D. Anther length: About 5.5 mm. Anther width: About 1 mm. Anther shape: Narrowly oblong. Anther color: Close to 155A. Pollen amount: Scarce. Pollen color: Close to 155D.

*Pistils.*—Quantity per flower: One. Pistil length: About 4 cm. Style length: About 3.8 cm. Style color: Close to NN155D. Stigma diameter: About 1 mm. Stigma shape: Club-shaped. Stigma color: Close to NN155D. Ovary color: Close to 144C.

*Seeds and fruits.*—Seed and fruit development have not been observed on plants of the new *Curcuma* to date.

Disease & pest resistance: To date, plants of the new *Curcuma* have not been observed to be resistant to pathogens or pests common to *Curcuma*.

Temperature tolerance: Plants of the new *Curcuma* have been observed to be tolerant to temperatures ranging from about 5° C. to about 40° C. and to be suitable for USDA Hardiness Zones 10 to 12.

It is claimed:

1. A new and distinct *Curcuma* plant named 'Curhalawi' as illustrated and described.

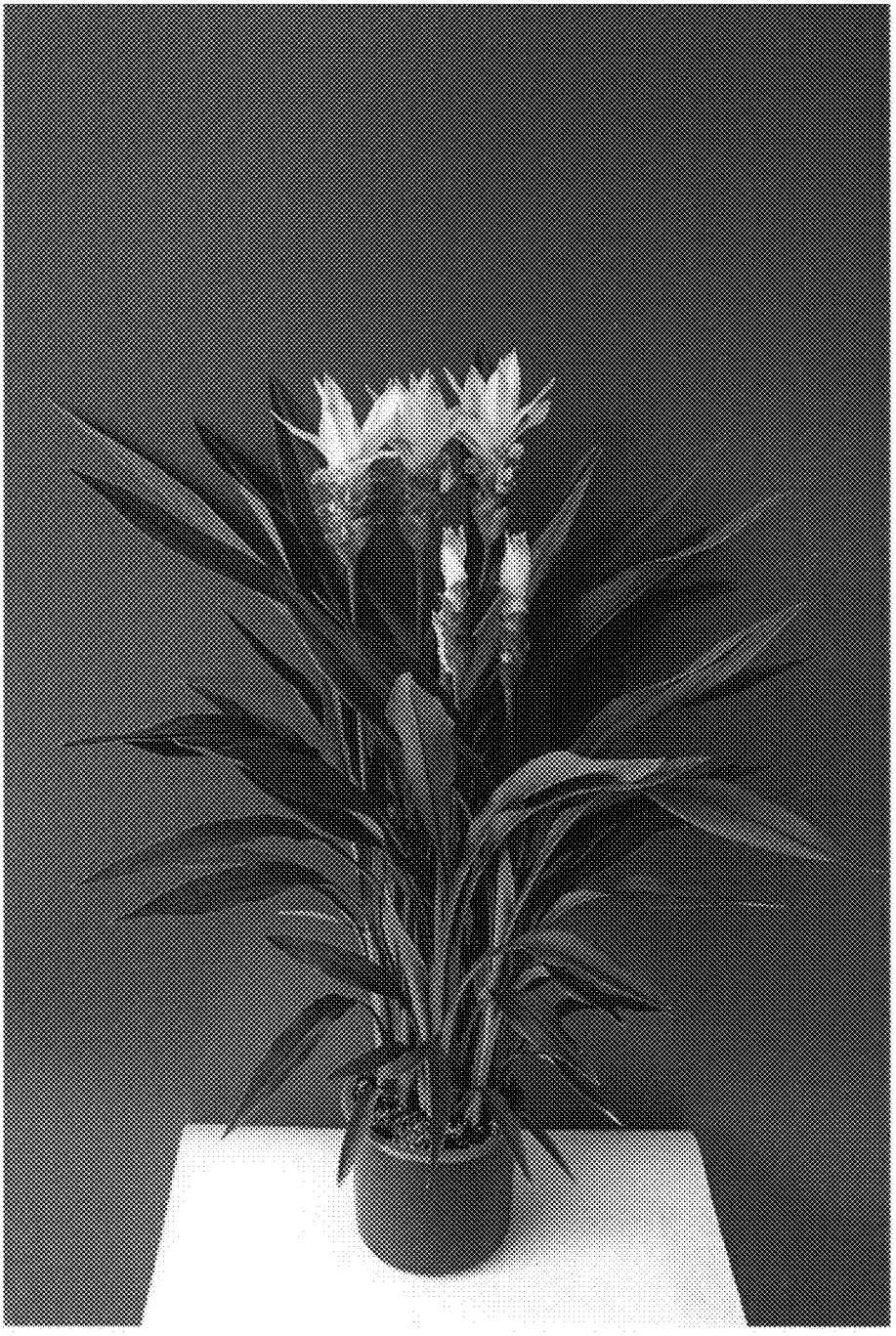

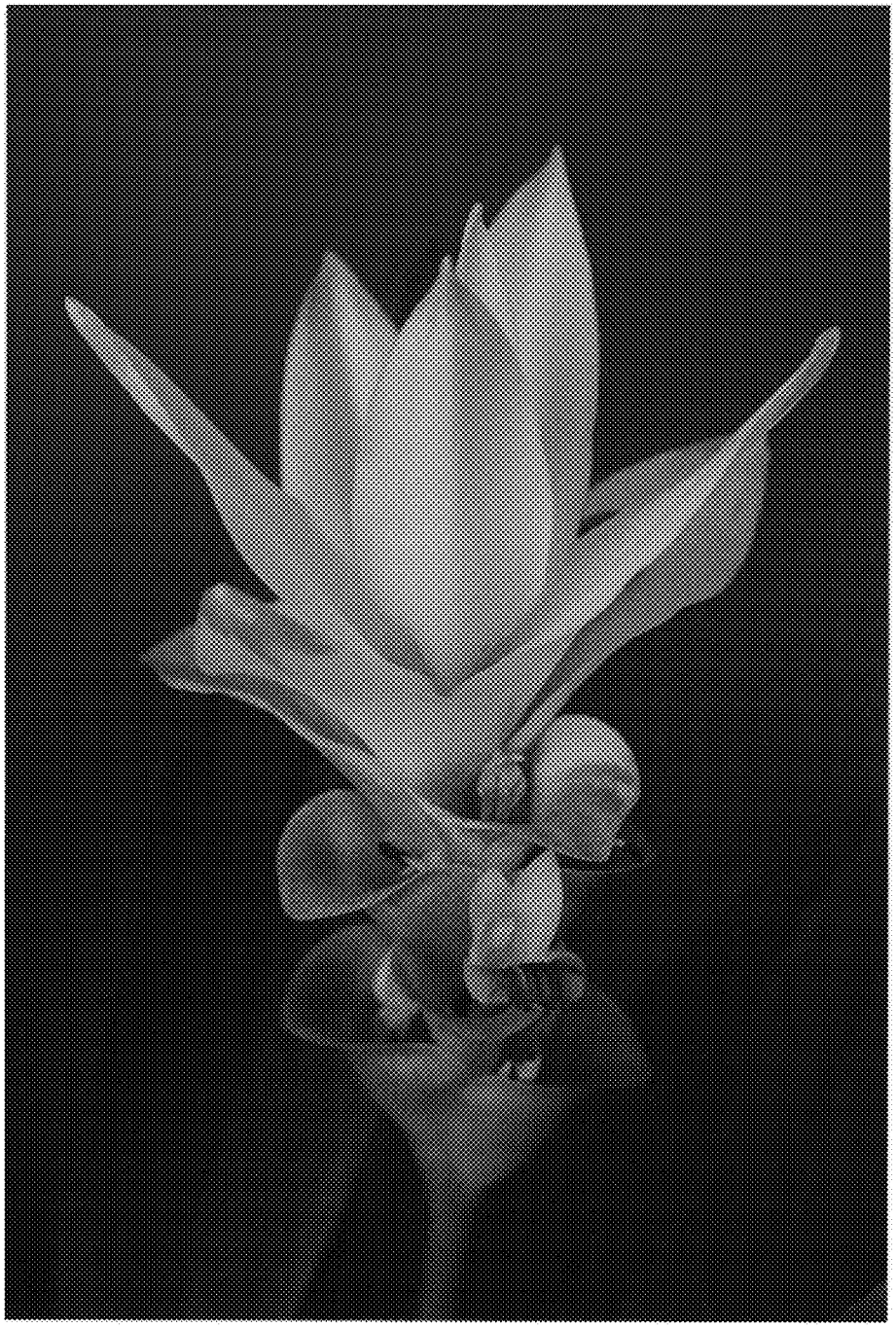

* * * * *